United States Patent [19]

Munir

[11] Patent Number: 4,788,145

[45] Date of Patent: Nov. 29, 1988

[54] PROCESS FOR PREPARING 1-O-ALPHA-D-GLUCOPYRANOSIDO-D-FRUCTOSE

[75] Inventor: Mohammad Munir, Kindenheim, Fed. Rep. of Germany

[73] Assignee: Suddeutsch Zucker Aktiengesellschaft, Mannheim, Fed. Rep. of Germany

[21] Appl. No.: 918,680

[22] Filed: Oct. 14, 1986

Related U.S. Application Data

[63] Continuation of Ser. No. 550,672, Nov. 10, 1983, abandoned, which is a continuation-in-part of Ser. No. 482,829, Apr. 7, 1983, abandoned, Continuation-in-part of Ser. No. 890,964, Jul. 29, 1986.

[30] Foreign Application Priority Data

Nov. 11, 1982 [DE] Fed. Rep. of Germany ....... 3241788

[51] Int. Cl.$^4$ ............................................. C12P 19/12
[52] U.S. Cl. .................................. 435/100; 435/822; 435/847; 435/881; 426/658; 426/48; 127/46.1; 127/53; 127/58
[58] Field of Search .................. 426/48, 658; 435/100, 435/881, 822, 847; 127/53, 58, 46.1

[56] References Cited

U.S. PATENT DOCUMENTS 4,378,434 3/1983 Prentice et al. ..................... 435/813
4,480,034 10/1984 Hsieh ................................. 435/813

FOREIGN PATENT DOCUMENTS 3038219 4/1982 Fed. Rep. of Germany ...... 435/100

OTHER PUBLICATIONS

Ziesenitz, Chemical Abstracts, 97: 37664y, p. 459 (1982).

Primary Examiner—Esther M. Kepplinger
Attorney, Agent, or Firm—Armstrong, Nikaido, Marmelstein & Kubovcik

[57] ABSTRACT

A process for preparing 1-O-α-glucopyranoside-D-fructose by enzymatically converting sucrose is described, wherein a sucrose solution is brought into contact with free or immobilized, living or dead whole cells or with microorganisms forming the free or immobilized enzyme extract of isomaltulose from saccharose, the solution so treated being next subjected to chromatographic separation at ion exchangers or other suitable separation materials to obtain the 1-O-α-D-glucopyranosido-D-fructose as an aqueous solution which is then converted by methods known per se into the dry form.

7 Claims, No Drawings

PROCESS FOR PREPARING 1-O-ALPHA-D-GLUCOPYRANOSIDO-D-FRUCTOSE

This application is a continuation of application Ser. No 550,672, filed Nov. 10, 1983, now abandoned, which in turn is a continuation-in-part of application Ser. No. 482,829, filed Apr. 7, 1983, now abandoned. This application is also a continuation-in-part of my copending application Ser. No. 890,964, filed July 29, 1986.

TECHNICAL FIELD

This invention relates to a process for preparing 1-O-α-D-glucopyranosido-D-fructose and, particularly, to a process for the enzymatic conversion of sucrose or isomaltulose into 1-O-α-D-glucopyranosido-D-fructose using microorganisms or an enzyme extracted therefrom. This invention also relates to the use of 1-O-α-D-glucopyranosido-D-fructose as a sweetener.

BACKGROUND ART

G. Avidad (Biochem. J. 73, 587 [1959]) has reported obtaining 1-O-α-D-glucopyranosido-D-fructose by the action of yeast on a mixture of sucrose and fructose. The yield, however, was very low (0.77% based on the starting sucrose). B. M. Lund and G. M. Wyatt (J. Gen. Microbiol. 78 [Pt. 2], 331–6 [1973]) were able to prepare 1-O-α-D-fructose in addition to 6-O-α-D-glucopyranosido-D-fructose (isomaltulose) by the action of *Erwinia carotovora atroseptica* on nutrient solutions containing 2–4% of sucrose.

These preparation methods suffer from the disadvantage of very low yields, so that industrial use of the methods has not been possible.

The German Offenlegungsschrift No. 30 38 219 discloses that 1-O-α-D-glucopyranosido-D-fructose is formed as a byproduct in the preparation of isomaltulose (6-O-α-D-glucopyranosido-D-fructose) by enzymatic conversion from sucrose using immobilized bacterial cells.

DISCLOSURE OF INVENTION

It has now been found that by observing proper conditions of the reaction, a product solution can be prepared from both a sucrose solution and an isomaltulose solution using microorganisms which form isomaltulose from sucrose, the product solution surprisingly containing 1-O-α-D-glucopyranosido-D-fructose as the main component. It is immaterial in this respect whether the microorganisms are used as whole cells in living or dead form or if the cells are free or immobilized, or whether the enzyme is first derived from the cells and is then used as a free enzyme or in immobilized form.

The process of the present invention for preparing 1-O-α-D-glucopyranosido-D-fructose by enzymatic conversion from sucrose or isomaltulose is characterized in that a solution of sucrose or isomaltulose is brought into contact with free or immobilized, living or dead, whole cells or with free or immobilized enzyme extract of microorganisms which form isomaltulose from sucrose; the 1-O-α-D-glucopyranosido-D-fructose is first obtained by chromatographic separation with ion exchangers or other suitable separation materials as an aqueous solution, and in that it is then converted to a dry form by methods known per se.

In the process of the present invention solutions of sucrose or isomaltulose, preferably in concentrations of about 20 to 55% by weight are treated with the free or immobilized cells or enzyme extract of the microorganisms at a temperature of from 25° to 55° C. and preferably, 30° to 50° C. and for a time to obtain a sufficient conversion of the sucrose or isomaltulose to the desired sugar. The contact time is at least 10 to 20 hours, and preferably at least 15 to 18 hours for sucrose solutions. Longer contact times may be required for solutions of isomaltulose.

The conversion of the sucrose or isomaltulose solution can be carried out either continuously or batchwise in any appropriate reactor such as, for example, in a fermenter or, particularly when using immobilized cells or enzyme extract, in a column filled with the immobilized cells or enzyme extract.

As the microorganisms useful in the process of the present invention, either as living or dead cells or in the form of an enzyme extract, and whether free or immobilized, there may be employed any of the microorganisms capable of enzymatically converting sucrose into isomaltulose. These include *Protaminobacter rubrum* (CBS 574.77), *Serratia plymuthica* (ATCC 15928), *Serratia marcescens (NCIB* 82285), *Leuconostoc mesenteroides* (NRRL B-512 F [ATCC 10830a]) and *Erwinia rhapontici (NCPPB* 1578). Cells or enzyme extract of *Protaminobacter rubrum* (CBS 574.77) are preferably employed.

To produce the cells which can then be immobilized or subjected to enzyme extraction for the process of the invention, an optimal cell multiplication takes place in a nutrient medium containing only 5% by weight of dry substance content. The nutrient medium contains a syrup (an intermediate product of the sugar industry), corn steep liquor and $(NH_4)_2HPO_4$. However, using a substantially more economical nutrient substrate consisting only of sugar beet molasses and $(NH_4)_2HPO_4$ is advantageous. To prepare this nutrient substrate, the molasses is diluted with distilled water to a content of 5% by weight of dry substance. 0.1 kg of $(NH_4)_2HPO_4$ are added as an additional source of nitrogen and phosphate to 100 kg of this solution. The pH value is adjusted to 7.2 by means of caustic soda or caustic potash or with hydrochloric acid.

The inoculum of an isomaltulose-forming microorganism, for instance, *Protaminobacter rubrum* (CBS 574.77), is transferred with 10 ml of sterile nutrient substrate of the above composition to a shake-flask and incubated in 200 ml of the same nutrient medium at 29° C. As soon as the cell count in the agitated culture reaches $5 \times 10^9$ cells/ml, the culture is transferred into a small fermenter together with nutrient medium of the above composition and is made to multiply at the maximum possible aeration and stirring rate at 29° C. The multiplication is controlled in the same manner as for the agitation culture by the determination of the cell count. As soon as the cell count reaches $5 \times 10^9$ cells/ml, the fermenter can be harvested.

Immobilization of the cells may be carried out according to any of the methods cited by I. CHIBATA (Immobilized enzymes, John Wiley and Sons, New York, London, 1978) for immobilizing entire cells. Methods which were found to be specially applicable include flocculation with a cationic flocculent; flocculation with chitosan; inclusion into a calcium alginate matrix, inclusion into cellulose diacetate or cellulose triacetate; inclusion into a K-carrageenan gel; and a flucculation with a cationic flocculent or an anionic flocculent or a combination of both of these.

To prevent leakage of the cells, the preparations made by the above methods require cross-linking. Bifunctional reagents are used for cross-linking, for instance, glutaraldehyde. It is not possible to use the conventionally employed glutaraldehyde concentration of 2.5 to 5% for a contact time of 30 to 45 minutes as regards isomaltulose-forming microorganisms. It was found that under these conditions all the immobilized preparations were wholly inactivated. The optimal cross-linking conditions for the present method were found to be a concentration of 0.1% of glutaraldehyde and a treatment time of 10 minutes.

The enzymes useful in the process of the present invention may be extracted from the isomaltulose forming microorganisms by means which are also well-known in the art including, for example, decomposition, ammonium-sulfate precipitation and gel chromatography. Methods of immobilization of the enzymes which are also known per se can be used to prepare suitable immobilized enzymes.

The immobilized cells or enzymes may be placed into a suitable column reactor. This reactor should be heatable and of a diameter-to-bed height ratio of about 1:1 to 1:20, preferably 1:1 to 1:10, and, in particular, 1:1.5 to 1:5. The sucrose or isomaltulose solution is pumped at a temperature of 25° to 55° C., either from top to bottom or from the bottom to the top of the column. The flow rate is adjusted to obtain an appropriate contact time, for exmple, 10 to 20 hours.

Other features of the process according to the process of the invention may be better understood by referring to the preferred modes of the invention described in conjunction with the examples of set forth later in this specification.

The 1-O-α-D-glucopyranosido-D-fructose obtained with the process of the present invention can be used as a sweetener for foodstuffs, delicacies and feeds (a) in solid or liquid form; and/or (b) as a mixture with sweeteners of specific sweetness or sweetening power, equal to or higher than that of sucrose;

(c) as a mixture with fructose, sorbitol, xylitol, palatinit ® or other disaccharide alcohols of specific sweetness comparable to that of sucrose; or (d) as a mixture with isomaltulose with a solubility comparable to that of sucrose.

As determined in comparative taste tests, the specific sweetness of 1-O-α-D-glucopyranosido-D-fructose is 45% of that of sucrose and is equal to that of isomaltulose.

Compared to sucrose or isomaltulose, the solubility of 1-O-α-D-glucopyranosido-D-fructose in water is especially high. For instance 2 g of sucrose, 0.6 g of isomaltulose, but more than 4 g of 1-O-α-D-glucopyranosido-fructose will dissolve in 1 g of water at 20° C. Therefore, it is posible, for example, to avoid disadvantages relating to the lower solubility of isomaltulose by using a mixture of isomaltulose and 1-O-α-D-glucopyranosido-D-fructose. Initial research appears to confirm that due to the slight acid-formation following incubation with streptococcus mutans this sugar should be classified as non-cariogenetic. Furthermore, it does not appear to affect the formation of plaque polysaccharides. Also, 1-O-α-D-glucopyranosido-D-fructose is only split with difficulty by the human small intestine and therefore it is resorbed only partially and with a delay.

BEST MODES FOR CARRYING OUT INVENTION

The process of the invention is discussed comprehensively below in conjunction with the following examples.

EXAMPLE 1

(a) Cells from an inoculum of the *Protaminobacter rubrum* strain (CBS 574.77) are suspended in 10 ml of a sterile nutrient substrate consisting of 8 kg of thick juice from a sugar plant (dry substance content=65%), 2 kg of corn steep liquor, 0.1 kg of $(NH_4)_2HPO_4$ and 89.9 kg of distilled water (adjusted, if needed, to a pH of 7.2). This suspension is used as the inoculating material for the agitator preculture in 1-liter flasks with 200 ml each of the nutrient solution of the above composition. 20 such flasks (total content=4 liters) are incubated for 30 hours at 29° C. Thereafter, 16 liters of nutrient solution of the above composition are inoculated in a 30-liter small fermenter with the contents of the above 20 flasks and are fermented at 29° C. at an aeration rate of 20 liters/minute and a stirring rate of 350 rpm. The growing cell count is determined with a microscope. After reaching a cell count exceeding $5 \times 10^9$ cells/ml, fermentation is stopped by stopping agitation and aeration and by lowering the temperature to 20° C. The fermenter contents remain in the fermenter under sterile conditions and are used as the source of enzymes of the examples below.

(b) Near the end of the fermentation in Example 1(a), the following composition of the dry substance content is ascertained:

| | |
|---|---|
| fructose | 2-4% by weight |
| glucose | 0.5-1% by weight |
| sucrose | 5-10% by weight |
| isomaltulose | 75-85% by weight |
| 1-O—α-D-glucopyrano-sido-D-fructose | 5-10% by weight |
| oligomers | 0.5-2% by weight |

If this fermenter liquor is incubated for an additional 4 hours at 30° C. with slow agitation but without aeration, the following composition is obtained:

| | |
|---|---|
| fructose | 5-8% by weight of dry substance content |
| glucose | 2-5% by weight of dry substance content |
| sucrose | 0-0.5% by weight of dry substance content |
| 1-O—α-D-glucopyrano-sido-D-fructose | 10-20% by weight of dry substance content |
| isomaltulose | 65-72% by weight of dry substance content |
| oligomers | 3-6% by weight of dry substance content |

(c) The nutrient solution of Example 1(b) is separated from the cells by centrifuging and is evaporated to a dry substance content of 80% and is cooled with simultaneous addition of isomaltulose seed crystals in a cooling crystallizer at a rate of 1°-5° C./hour to a temperature of 20° C. The isomaltulose crystals generated are removed in a strainer-basket centrifuge. The mother liquor is again evaporated to a dry-substance content of 80% and cooled with addition of isomaltulose seed crystals in a cooling crystallizer at a rate of 0.5°-2° C./hour to 20° C. The generated isomaltulose crystals are separated in a strainer-basket centrifuge. This second mother liquor is evaporated to a dry-substance content of 85% and seeded with isomaltulose crystals. This syrup is diluted to about 1:1 by volume with methanol, ethanol or other alcohol and the alcoholic solution is cooled to 4° C. The crystallized isomaltulose is removed by centrifuging. This 3rd mother liquor has approximately the following dry substance content:

| fructose | 8–12% by weight |
|---|---|
| glucose | 4–6% by weight |
| sucrose | 0–2% by weight |
| isomaltulose | 45–50% by weight |
| 1-O—α-D-glucopyranosido-D-fructose | 30–35% by weight |
| oligomers | 3–6% by weight |

(d) The mother liquor obtained in Example 1(c) is freed of methanol by evaporation and is adjusted to a dry substance content of 15–20% and fermented with baker's yeast at 37° until no sucrose, glucose and fructose can be found in the solution. The yeast is separated. The clear solution is evaporated to a dry-substance content of 50% and then is subjected to separation by means of a chromatographic separation column. The fraction containing 1-O-α-D-glucopyranosido-D-fructose is collected and following full de-salting, the 1-O-α-D-glucopyranosido-D-fructose is obtained in dry form by crystallization, freeze-drying, spray-drying or other similar procedures.

(e) The fermentation of the mother liquor with yeast described in Example 1(d) is not mandatory. It may even be advantageous to forego such fermentation and to subject the mother liquor directly to chromatographic separation. In such an embodiment, methanol is removed from the mother liquor obtained per example 1(d) by evaporation, adjusted to a dry-substance content of 50% and then subjected to separation by a chromatographic separation column. The sugar, 1-O-α-D-glucopyranosido-D-fructose, is obtained in dry form from the fraction containing it after full de-salting by crystallization, freeze-drying, spray-drying or other similar procedures.

Yield: 14.3 kg per 100 kg of input sucrose.

The other sugars such as fructose, glucose and isomaltulose that accumulate in the chromatographic separation are not lost because they are useful in other respects (for instance, isomaltulose is used in preparing palatinit).

EXAMPLE 2

(a) The microorganisms used in this example are obtained by centrifuging the fermenter liquor of example 1(a) and are immobilized by methods known per se. The immobilized cells are placed in a temperature-controlled column; a sucrose solution (50% dry-substance content) continuously flows through these immobilized cells at 50° C. The flow rate is so adjusted that a mean residence time of 10 to 20 hours, preferably 15–18 hours is obtained. The following illustrative composition is determined in the product stream:

| fructose | 5.8% dry-substance content |
|---|---|
| glucose | 2.5% dry-substance content |
| sucrose | 0 dry-substance content |
| isomaltulose | 65.8 dry-substance content |
| 1-O—α-D-glucopyranosido-D-fructose | 23.2 dry-substance content |
| oligomers | 2.7 dry-substance content |

(b) The product solution is evaporated to 80% dry-substance content and with the addition of isomaltulose seed crystals is cooled in a cooling crystallizer at a cooling rate of 1°–5° C./hour to 20° C. The generated isomaltulose crystals are removed in a strainer-basket centrifuge. The mother liquor again is evaporated to a dry-substance content of 80% and is cooled with the addition of isomaltulose seed crystals in a cooling crystallizer at a cooling rate of 0.5°–2° C./hour to 20° C. The generated isomaltulose crystals are removed in a strainer-basket centrifuge. This second mother liquor is evaporated to a dry-substance content of 85% and seeded with isomaltulose crystals. This syrup is diluted by volume to about 1:1 with methanol, ethanol or other alcohol and the alcohol solution is cooled to 4° C. The crystallized isomaltulose is removed by centrifuging. The 3rd mother liquor so obtained has the following illustrative composition:

| fructose | 12.7% in dry substance |
|---|---|
| glucose | 5.5 in dry substance |
| sucrose | 0 in dry substance |
| isomaltulose | 25.0 in dry substance |
| 1-O—α-D-glucopyranosido-D-fructose | 50.9 in dry substance |
| oligomers | 5.9 in dry substance |

(c)(1) The mother liquor obtained per Example 2(b) is subjected to evaporation to remove the methanol, adjusted to a dry-substance content of 15–20% and fermented with baker's yeast at 37° C. until no sucrose, glucose or fructose is ascertained in the solution. The yeast is removed. The clear solution is evaporated to a dry-substance content of 50% and then is subjected to separation by means of a chromatographic separation column. The 1-O-α-D-glucopyranosido-D-fructose is obtained in dry form from the fraction containing it by crystallization, freeze-drying, spray-drying or other similar procedures.

(c)(2) The mother liquor obtained per Example 2(b) is subjected to evaporation to remove the methanol, adjusted to a dry-substance content of 50% and then is subjected to separation by means of a chromatographic separation column. The 1-O-α-D-glucopyranosido-D-fructose is obtained in dry form from the fraction containing it by crystallization, freeze-drying or other similar procedures.

Yield: 18.6 kg per 100 kg of input sucrose.

EXAMPLE 3

The microorganisms are obtained by centrifuging from the fermenter liquor obtained per Example 1(a) and the enzyme which forms isomaltulose from sucrose is isolated in pure form by methods known per se such as decomposition, ammonium-sulfate precipitation and gel chromatography. This enzyme is then immobilized by methods known per se.

The immobilized enzyme is placed in a temperature-controlled column reactor and a sucrose solution (50% dry substance content) is passed continuously through said enzyme at 50° C. The flow rate is adjusted in such a manner that a mean residence time of 10–20 hours, preferably 15–18 hours results.

The composition of the sugars in the product stream is nearly identical to that described in Example 2(a). This product solution is further processed as described in Examples 2(b) and 2(c). Accordingly, the yield of 1-O-α-D-glucopyranosido-D-fructose thus achieved is practically identical with that of Example 2, that is, it is about 18% referred to the input amount of sucrose.

EXAMPLE 4

Immobilized cells of Protaminobacter rubrum (CBS 574.77), prepared per Example 1(a) and immobilized by one of the methods of cell immobilization known per se are added to a temperature-controlled column reactor; and an isomaltulose solution at 50° C. and with a dry-substance content of 30% is continuously passed through said cells. The isomaltulose solution is made to circulate. The reaction continues until no more isomaltulose is present in the product stream. The total contact time amounts to about 150 hours. The product solution is determined to have the following composition:

| fructose | 31% of dry-substance |
|---|---|
| glucose | 31% of dry-substance |
| 1-O—α-D-glucopyrano-sido-D-fructose | 38% of dry-substance |

This product solution is evaporated to a dry-substance content of 50% and then is subjected to separation by means of a chromatographic separation column. The sugar, 1-O-α-D-glucopyranosido-D-fructose, is obtained in dry form from the fraction containing it by crystallization, freeze-drying, spray drying or other similar procedures.

It is also possible to avoid the chromatographic separation and to remove the companion sugars, fructose and glucose, using yeast. However, this approach is uneconomical because thereby two valuable sugars, namely fructose and glucose, will be destroyed.

Yield: about 38% of the input isomaltulose.

EXAMPLE 5

Use of the sugar, 1-O-α-D-glucopyranosido-D-fructose, in hard candy.
RECIPE:
25 kg of OF 1-O-α-D-Glucopyranosido-D-fructose
8 liters of water
1.2% acid (citric acid/tartaric acid = 1:1)
b 3% flavoring such as red-orange Silesia 111/658101 or Lemon Silesia 111/710134

The 1-O-α-D-glucopyranosido-D-fructose is dissolved in water and is boiled at 138° C. Thereafter the substance is placed on a cooling table and a mixture of acid, flavoring and coloring is worked-in. Then the substance is drawn several times from a hook and lastly it is shaped into candy.

EXAMPLE 6

Use of the sugar, 1-O-α-D-glucopyranosido-D-fructose, in ice cream
RECIPE:
3.6 kg of butter (83% fat)
12.5 kg of skimmed milk powder
15 kg of 1-O-α-D-glucopyranosido-D-fructose
0.6 kg of emulsifier (Cranodan TEF4, Grindsted)
68.3 kg of water.

The substance is first pasteurized at 78° C. and is then homogenzied in a two-stage procedure.

EXAMPLE 7

Use of the sugar, 1-O-α-D-glucopyranosido-D-fructose in jams.
RECIPE:
250 g of 1-O-α-D-glucopyranosido-d-fructose
450 g of fruit
5 g of amidated pectin
2.5 g of genugum (a trade name for k-Carrageenan)
4 g of citric acid
0.8 g of potassium sorbate
287.7 g of water
Dry-substance: 32%

First a pre-mixture is prepared from 1-O-α-glucopyranosido-D-fructose, amidated pectin, genugum, citric acid and potassium sorbate, which is then added to the comminuted fruit. The mixture is allowed to stand for 24 hours. After that, water is added and the mixture is boiled. following 4 minutes of boiling, the jam is filled into jars.

What is claimed is:

1. A process for preparing 1-O-α-D-glucopyranosido-D-fructose by the enzymatic conversion of isomaltulose, comprising contacting a 20–55% (w/w) aqueous solution of isomaltulose at a temperature of 25°–55° C. with a microorganism or an enzyme of a microorganism which forms isomaltulose from sucrose to form a first product solution containing isomaltulose and said 1-O-α-D-glucopyranosido-D-fructose; removing at least a portion of the isomaltulose from said first product solution by crystallization to form a mother liquor; and recovering said 1-O-α-D-glucopyranosido-D-fructose from the mother liquor.

2. The process of claim 1 wherein said microorganisms are living or dead and are free or immobilized.

3. The process of claim 1 wherein said enzyme is free or immobilized.

4. The process of claim 1 wherein said mother liquor is subjected to fermentation with free or immobilized yeast to ferment yeast-fermenting sugars contained in said mother liquor prior to recovery of said 1-O-α-D-glucopyranosido-D-fructose.

5. The process of claim 1 wherein the temperature is 30° to 50° C.

6. The process of claim 1 wherein said 1-O-α-D-glucopyranosido-D-fructose is recovered from the mother liquor by chromatographic separation.

7. The process of claim 1 wherein the aqueous solution of isomaltulose is contacted with said microorganism or enzyme for at least 10 hours.

* * * * *